(12) United States Patent
Zhu et al.

(10) Patent No.: US 8,961,587 B2
(45) Date of Patent: Feb. 24, 2015

(54) BRANCHED STENT GRAFT

(75) Inventors: Qing Zhu, Shanghai (CN); Qiyi Luo, Shanghai (CN); Zhenyu Yuan, Shanghai (CN)

(73) Assignee: Microport Endovascular (Shanghai) Co., Ltd., Shanghai (CN)

( * ) Notice: Subject to any disclaimer, the term of this patent is extended or adjusted under 35 U.S.C. 154(b) by 150 days.

(21) Appl. No.: 13/254,010

(22) PCT Filed: Mar. 17, 2010

(86) PCT No.: PCT/CN2010/071099
§ 371 (c)(1),
(2), (4) Date: Aug. 31, 2011

(87) PCT Pub. No.: WO2010/105561
PCT Pub. Date: Sep. 23, 2010

(65) Prior Publication Data
US 2011/0319983 A1    Dec. 29, 2011

(30) Foreign Application Priority Data

Mar. 18, 2009    (CN) .......................... 2009 1 0047748

(51) Int. Cl.
*A61F 2/06*    (2013.01)
*A61F 2/07*    (2013.01)
(Continued)

(52) U.S. Cl.
CPC ............. *A61F 2/07* (2013.01); *A61F 2002/065* (2013.01); *A61F 2002/826* (2013.01); *A61F 2/89* (2013.01); *A61F 2002/075* (2013.01); *A61F 2220/0075* (2013.01)
USPC ........ 623/1.35; 623/1.13; 623/1.16; 623/1.34

(58) Field of Classification Search
CPC ................................................ A61F 2002/821
USPC ...................... 623/1.13, 1.16, 1.35
See application file for complete search history.

(56) References Cited

U.S. PATENT DOCUMENTS

| 6,183,481 B1 | 2/2001 | Lee et al. |
| 6,514,281 B1 | 2/2003 | Blaeser et al. |

(Continued)

FOREIGN PATENT DOCUMENTS

| CN | 2453960 | 10/2001 |
| CN | 2635119 | 8/2004 |

(Continued)

OTHER PUBLICATIONS

PCT/CN2010/071099 International Search Report and Written Opinion dated Jun. 17, 2010 (9 pages).

(Continued)

*Primary Examiner* — Bruce E Snow
*Assistant Examiner* — Brian Dukert
(74) *Attorney, Agent, or Firm* — Michael Best & Friedrich LLP (57) ABSTRACT

A branched stent graft comprises a main body portion and a branch portion. Each of the main body portion and the branch portion includes a stent and a tubular graft. The stent of the main body portion includes a plurality of stent segments, at least one of which is a varying-height stent segment (102). The stent of the branch portion includes one or more stent segments, at least one of which is a varying-height stent segment (103). The distance between the proximal-most stent segment of the branch portion and the main body portion is in the range of 2-8 mm. A positioning ring (105) may be used at a side opening which connects the branch portion and the main body portion, and the positioning ring (105) can be sutured inside the graft of the main body, between the graft of the main body and the graft of the branch, or outside the graft of the branch.

11 Claims, 6 Drawing Sheets

(51) Int. Cl.
    *A61F 2/82*       (2013.01)
    *A61F 2/89*       (2013.01)

(56) References Cited

U.S. PATENT DOCUMENTS

| | | | |
|---|---|---|---|
| 6,551,350 | B1 | 4/2003 | Thornton et al. |
| 6,663,665 | B2 | 12/2003 | Shaolian et al. |
| 6,908,477 | B2 | 6/2005 | McGuckin, Jr. et al. |
| 6,951,572 | B1 | 10/2005 | Douglas |
| 7,425,219 | B2 | 9/2008 | Quadri |
| 2003/0236565 | A1 | 12/2003 | DiMatteo |
| 2004/0098084 | A1 | 5/2004 | Hartley et al. |
| 2004/0243221 | A1 | 12/2004 | Fawzi et al. |
| 2006/0004433 | A1 | 1/2006 | Greenberg et al. |
| 2006/0178726 | A1 | 8/2006 | Douglas |
| 2008/0077227 | A1 | 3/2008 | Ouellette et al. |
| 2008/0109065 | A1 | 5/2008 | Bowe |
| 2008/0195191 | A1* | 8/2008 | Luo et al. ............ 623/1.13 |
| 2008/0312732 | A1* | 12/2008 | Hartley et al. ............ 623/1.13 |
| 2012/0101563 | A1 | 4/2012 | Zhu et al. |

FOREIGN PATENT DOCUMENTS

| | | |
|---|---|---|
| CN | 2673332 | 1/2005 |
| CN | 2675083 | 2/2005 |
| CN | 2920188 | 7/2007 |
| CN | 101015478 | 8/2007 |
| CN | 101152109 | 4/2008 |
| CN | 201131823 | 10/2008 |
| WO | 2004089249 | 10/2004 |
| WO | 2005037141 | 4/2005 |
| WO | 2006028925 | 3/2006 |

OTHER PUBLICATIONS

PCT/CN2010/071099 International Preliminary Report on Patentability dated Jun. 17, 2010 (5 pages).
PCT/CN2010/072280 International Search Report and Written Opinion dated Jul. 29, 2010 (1 page).
United States Patent Office Action for U.S Appl. No. 13/322,256 dated Jun. 24, 2013 (9 pages).
United States Patent Office Action for U.S. Appl. No. 13/322,256 dated Jan. 27, 2014 (10 pages).

* cited by examiner

FIG. 12

BRANCHED STENT GRAFT

CROSS-REFERENCE TO RELATED APPLICATIONS

This application is a national stage filing under 35 U.S.C. 371 of International Application No. PCT/CN2010/071099, filed Mar. 17, 2010, which claims priority benefits to Chinese Patent Application No. 200910047748.6, filed Mar. 18, 2009. These applications are incorporated herein by reference in their entirety.

TECHNICAL FIELD

The present invention relates to a minimally invasive medical device for treating aortic diseases and, in particular, to a branched stent graft.

BACKGROUND ART

In recent years, advances in aortic surgery have led to the use of stent grafts in the treatment of aortic disease. Stent grafts may be used in the treatment of aortic dissecting aneurysms, aortic true aneurysms, aortic pseudoaneurysms, aortic penetrating ulcers, etc. The application of this technique greatly reduces the mortality compared to conventional operative treatments, greatly reduces the occurrence of postoperative complications, minimizes operation incisions, and insures a more rapid recovery for the patient. Using the treatment of aneurysm as an example, the stent graft is expanded after being placed at the location of the lesion in order to isolate the tumor body from the blood. This eliminates the risk of death caused by massive hemorrhaging due to the rupture of the aneurysm, and also prevents tissue and organs from being compressed by the tumor body. Several products are already presently being used at home as well as abroad, for example Talent, AneuRex, Exclude, Relay, Gore, etc., abroad, and Hercules, Aegis, Ankura, etc. at home.

However, most of the above products are in a straight cylindrical shape, and have no branches at proximal ends thereof to assist in anchoring, and thus can only perform positioning using the bare segment, the small wave segment and the large wave segment in the main body. Therefore, the above products need enough anchoring distance. Otherwise, a risk of stent shift down and endoleak will be produced. Thereby, the above products are only adapted to the descending thoracic aortic aneurysm, and usually require a normal thoracic aortic aneurysm wall where the aneurysm or the tear is at least 15 mm away from the left subclavian artery. With respect to the cases of the dissection or aneurysm involving the left subclavian artery, a left subclavian artery bypass surgery is generally performed, and then the above stent graft is applied to treat the aneurysm or dissection rupture. However, such a method still causes comparatively high endoleak complications. With respect to the patients having the dissection or the aneurysm which involves the range from the ascending aortic aneurysm to the left common carotid artery, no available stent graft exists at present, and a conventional operative treatment method is still employed.

The design and use of the stent graft with a branch may be able to eliminate the need for conventional operative treatments. The main body portion and the branch portion of the stent can be respectively used for repairing the lesions in the aorta and the branch artery. CN201131823Y discloses an endovascular stent with a branch, where the stent segments of the main body and the branch of the stent are single in structure and cannot be adapted to diversified blood vessel shapes. CN101015478A also discloses a branched stent graft, where the branch portion of the stent is connected with the main body portion via a flexible connecting part, and the main body portion and the branch portion are respectively used for the aorta and the left subclavian artery. This stent graft can ensure blood supply to the aorta and the left subclavian artery at the same time; however, if the release of the proximal flexible connecting part of the branch is unfavorable (e.g., distorted or folded), the left subclavian artery will be blocked. Accordingly, the above stent grafts with a branch in the prior art have a limited application range and can generally only be used for lesions in the left subclavian artery, while doing nothing for lesions in the bow and the ascending aorta or lesions involving multiple branches.

SUMMARY OF THE INVENTION

Figure 1:
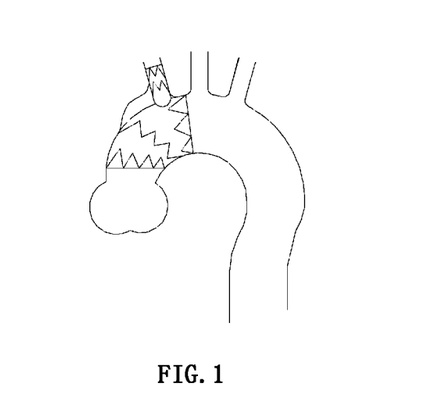
FIG. 1 is a schematic diagram of the service state of the branched stent graft of the present invention.

The object of the present invention is to provide a branched stent graft, which is stable in structure, possesses significant bending properties, and has also been adapted to treating aortic diseases involving the branch artery (e.g., aortic aneurysm). The service state of the branched stent graft is shown in FIG. 1.

The branched stent graft provided by the present invention comprises a main body portion and a branch portion, each of the main body portion and the branch portion including a stent and a tubular graft sutured with the stent, and the graft of the branch portion being sutured with the graft of the main body portion, wherein the stent of the main body portion includes a plurality of stent segments, at least one of which is a varying-height stent segment; the stent of the branch portion includes one or more stent segments, at least one of which is a varying-height stent segment, and the distance between the proximal-most stent segment of the branch portion and the main body portion is in the range of 2-8 mm; wherein the varying-height stent segment refers to a stent segment, in which, after a cylindrical single coil forming the stent segment is deployed, all the wave troughs of the waveform thereof are on the same horizontal line, and not all the wave crests are on the same horizontal line.

Figure 2:
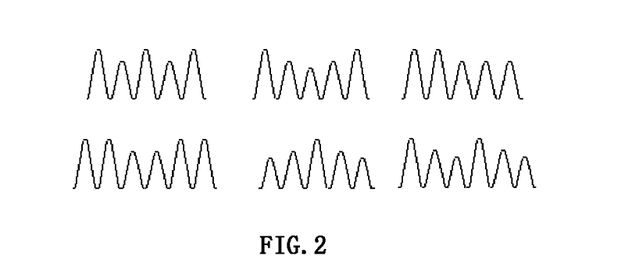
FIG. 2 is a schematic diagram of the preferred varying-height stent segments after expansion.

Preferably, the waveform of the varying-height stent segment of the main body portion and/or the branch portion after its cylindrical single coil is deployed is one or more of the waveforms as shown in FIG. 2.

Preferably, the main body portion includes at least one equal-height stent segment, wherein the equal-height stent segment refers to a stent segment, in which, after a cylindrical single coil forming the stent segment is deployed, all the wave troughs of the waveform thereof are on the same horizontal line, and all the wave crests are also on the same horizontal line.

Preferably, the proximal-most and/or distal-most stent segment of the main body portion is the equal-height stent segment.

Preferably, the number of the branch portions is 1, 2, or 3.

Preferably, the stent segment(s) of the branch portion is(are) sutured outside the graft.

Preferably, the stent segments of the main body portion are sutured inside the graft, or the proximal and distal stent segments of the main body portion are sutured inside the graft but the intermediate stent segment(s) of the main body portion is(are) sutured outside the graft.

Preferably, the graft of the main body portion has a length in the range of 40-133 mm and a diameter in the range of 16-36 mm; the number of the stent segments of the main body portion is in the range of 3-7, wherein a distance between the stent segments is in the range of 1-5 mm; the graft of the branch portion has a length in the range of 13-30 mm and a diameter in the range of 6-14 mm; the number of the stent segments of the branch portion is in the range of 1-2, wherein a distance between the stent segments is in the range of 1-5 mm; and the distance between the proximal-most stent segment of the branch portion and the main body portion is in the range of 2-4 mm.

Preferably, the main body portion and the branch portion are further sutured with radiopaque markers.

Figure 3:
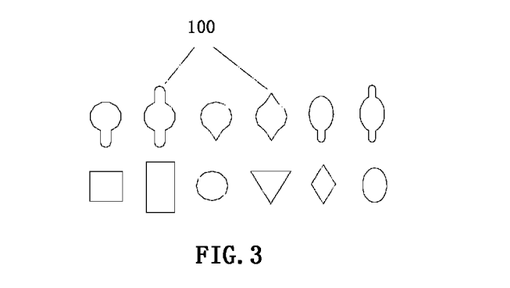
FIG. 3 is a schematic diagram of the positioning rings.

Preferably, a positioning ring is used at a side opening which connects the branch portion and the main body portion, the positioning ring is sutured inside the graft of the main body, between the graft of the main body and the graft of the branch, or outside the graft of the branch, and the shape of the positioning ring is one of the shapes as shown in FIG. 3.

Preferably, the positioning ring is provided with a flange 100, and the flange 100 is provided in an axial direction of the main body portion.

Preferably, the stent is made of a material having a good biological compatibility and support force, e.g., a shape memory alloy, a 316L medical stainless steel, a Ni-based alloy (e.g., nickel-titanium wires), a Co-based alloy, or a degradable or nondegradable polymer material.

Preferably, the graft is made of a polymer material having a biological compatibility, e.g., polytetrafluoroethylene, a polyester textile, a polyamide textile, a polypropylene textile, etc.

Preferably, the radiopaque markers are made of a platinum-iridium alloy, pure platinum, pure gold, a NiTi shape memory alloy or a stainless steel.

Preferably, the positioning ring is made of a metallic or non-metallic material, e.g., nickel-titanium wires, stainless steel wires, nylon or polyurethane.

The definitions of the terms concerned in the present invention are as follows:

the "proximal end" refers to a side of the stent graft close to the heart;

the "distal end" refers to a side of the stent graft away from the heart;

the "wave crest" refers to the most protruding portion of the single waveform of the stent segment towards the proximal end;

the "wave trough" refers to the most protruding portion of the single waveform of the stent segment towards the distal end;

the "distance between the proximal-most stent segment of the branch portion and the main body portion" refers to the shortest distance between the most protruding wave crest of the stent segment towards the proximal end and the main body portion;

the "distance between the stent segments" refers to the distance between the adjacent stent segments, and in particular, refers to the shortest distance between the most protruding wave crest of one stent segment towards the proximal end and the plane on which all the wave troughs of the proximal stent segment adjacent to the above stent segment are located; and the "side opening refers to an opening at the joint of the branch portion and the main body portion.

With regard to the branched stent graft of the present invention, the main body portion and the branch portion are designed as one piece, which facilitates the reduction of difficulty in alignment and positioning in the implanting process, and can avoid the risk of endoleak from where the main body portion and the branch portion are joined.

The main body portion employs the varying-height stent segments, which facilitates the adaptation of the main body portion to distortions of different forms of the aorta in three-dimensional directions.

The branch portion employs the varying-height stent segment, and the proximal-most stent segment of the branch portion and the main body portion are spaced apart by a gap of 2-8 mm, which facilitates a 360° free rotation of the branch, so that the branch portion is adapted to distortions of different forms of the branch of the aorta in three-dimensional directions, and which meanwhile facilitates a sufficient expansion of the stent to avoid the risk of causing thrombus due to a non-fluent blood flow at the branched blood vessel to lead to an insufficient blood supply or embolization of the blood vessel of the brain. The design of the branch further facilitates the increase of the anchoring force of the stent of the main body to achieve an effective block of the aneurysm.

The proximal-most end and the distal-most end of the main body portion are respectively provided with an equal-height stent segment, which facilitates a secure attachment of the stent so as to effectively reduce the risk of the occurrence of endoleak.

The number of the branches can be designed as 1, 2, or 3 according to actual requirements, wherein a single branch can be used for the brachiocephalic and the left subclavian artery, the double branches can be used for cases involving the brachiocephalic and the left common carotid artery or involving the left common carotid artery and the left subclavian artery, and the three branches can be used for cases of the aneuysm involving the brachiocephalic, left common carotid artery and the left subclavian artery.

The stent segment of the branch portion is sutured outside the graft, which facilitates maximization of the retention of the blood flow passage of the blood vessel of the branch to reduce the risk of the formation of thrombus.

The stent segments of the main body portion are sutured inside the graft, which facilitates the improvement of the adherent property of the graft to reduce the risk of endoleak; or the proximal and distal parts of the main body portion are sutured inside the graft, which facilitates the improvement of the adherent property of the graft to reduce the risk of endoleak; and the stent segments near the intermediate part of the stent segments of the main body are sutured outside the graft, which facilitates the reduction of the risk of the formation of thrombus.

The main body portion and the branch portion are sutured with radiopaque markers which are helpful to accurately position the main body and the branch of the stent during the introduction process to avoid an unfavorable conduction or even block of the blood vessel of the branch due to an inaccurate positioning of the branch.

A positioning ring is used at the side opening, which enhances the expanding capacity of the side opening, so that the branch may keep patency to avoid the risk of an incomplete expansion of the branch due to influences by bad factors such as torsion or calcification of the blood vessel at the joint.

If the edge of the positioning ring is provided with a flange 100, the flange 100 should be provided in the axial direction of the stent to reduce the crimping diameter at the installation of the stent.

The branched stent graft of the present invention may be used for treating the ascending aortic aneurysm, the aortic arch aneurysm, the descending aortic aneurysm and the dissection rupture thereof. The stent can be implanted into the aorta and the branch artery (e.g., the left subclavian artery, the left common carotid artery or the brachiocephalic) at the same time to treat the dissection rupture and the aneurysm involving the ascending aortic aneurysm, the aortic arch and the descending aortic aneurysm. The present invention eliminates the limitations of the products in the prior art, substantially avoids conventional operative treatments for such diseases, and broadens indications.

BRIEF DESCRIPTION OF THE DRAWINGS

By the reading of the following detailed descriptions of the non-restrictive embodiments made by the figures, the other features, the object and the advantages of the present invention will become more obvious.

DETAILED DESCRIPTION

Embodiment 1

Figure 4:
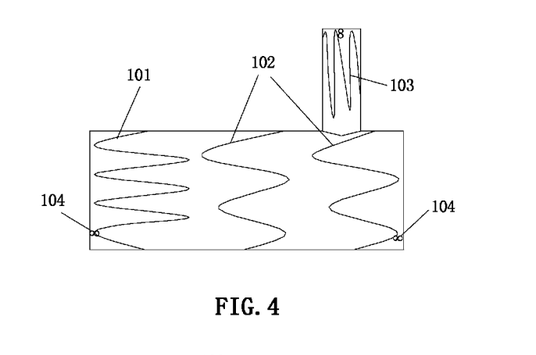
FIG. 4 is a schematic diagram of the branched stent graft of Embodiment 1.
Figure 6:
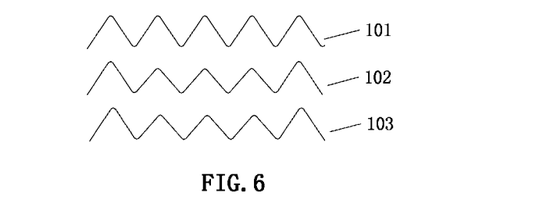
FIG. 6 is a schematic diagram of the stent segments of the branched stent grafts of Embodiments 1 and 2 after expansion.

Single Branched Stent Graft (See FIGS. 4 and 6)

Main Body Portion

The graft of the main body is made of a polyester textile, and has a length of 40 mm and a diameter of 16 mm. The stent of the main body is made of NiTi wires and has a diameter of 0.016". The stent of the main body includes three stent segments, which are in turn an equal-height stent segment 101, a varying-height stent segment 102 and a varying-height stent segment 102 from the proximal end to the distal end (the left of the figure is the proximal end of the main body). The equal-height stent segment 101 includes six waveforms, wherein the height difference between the wave crest and the wave trough is 12 mm. The varying-height stent segment 102 includes five waveforms, wherein with respect to the two waveforms at both ends, the height difference between the wave crest and the wave trough is 12 mm, and with respect to the intermediate three waveforms, the height difference between the wave crest and the wave trough is 10 mm. The expansion diagrams of these stent segments are shown in FIG. 6. Each of the stent segments of the main body portion is sutured inside the graft of the main body, and the distance between the stent segments is 4 mm. The distal and proximal ends of the main body are sutured with several radiopaque markers 104, which are made of a platinum-iridium alloy, and take on a shape of the digit "8" having a height of 3 mm and a width of 1.5 mm.

Branch Portion

The graft of the branch is made of a polyester textile, and has a length of 15 mm and a diameter of 6 mm. The stent of the branch is made of NiTi wires and has a diameter of 0.014". The stent of the branch includes one varying-height stent segment 103 (the top of the figure is the distal end of the branch). The varying-height stent segment 103 includes five waveforms, wherein with respect to the two waveforms at both ends, the height difference between the wave crest and the wave trough is 12 mm, and with respect to the intermediate three waveforms, the height difference between the wave crest and the wave trough is 10 mm. The expansion diagram of this stent segment is shown in FIG. 6. This stent segment is 3 mm away from the main body portion, the varying-height stent segment 103 is sutured outside the graft of the branch, and the center of the branch is 32 mm away from the proximal end of the main body. The branch is sutured with several radiopaque markers 104.

Embodiment 2

Figure 5:
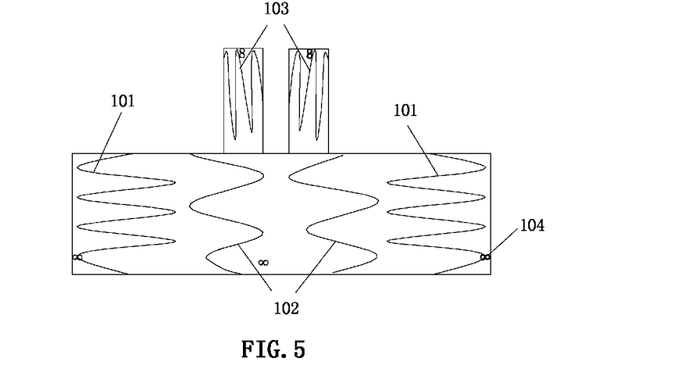
FIG. 5 is a schematic diagram of the branched stent graft of Embodiment 2.

Double Branched Stent Graft (See FIGS. 5 and 6)

Main Body Portion

The graft of the main body is made of a polyester textile, and has a length of 53 mm and a diameter of 16 mm. The stent of the main body is made of NiTi wires and has a diameter of 0.016". The stent of the main body includes four stent segments, which are in turn an equal-height stent segment 101, two varying-height stent segments 102 and an equal-height stent segment 101 from the proximal end to the distal end (the left of the figure is the proximal end of the main body). The expansion diagrams of these stent segments are shown in FIG. 6. Each of the stent segments of the main body is sutured inside the graft of the main body, and the distance between the stent segments is 4 mm. The distal and proximal ends of the main body are sutured with several radiopaque markers 104.

Branch Portion

The graft of the branch is made of a polyester textile, and has a length of 15 mm and a diameter of 6 mm. The stent of the branch is made of NiTi wires and has a diameter of 0.014". The stent of the branch includes one varying-height stent segment 103 (the top of the figure is the distal end of the branch). The expansion diagram of this stent segment is shown in FIG. 6. This stent segment is 3 mm away from the main body portion, the varying-height stent segment 103 is sutured outside the graft of the branch, and the centers of the double branches are respectively 20 mm and 30 mm away from the proximal end of the main body. The branch is sutured with several radiopaque markers 104.

Embodiment 3

Figure 7:
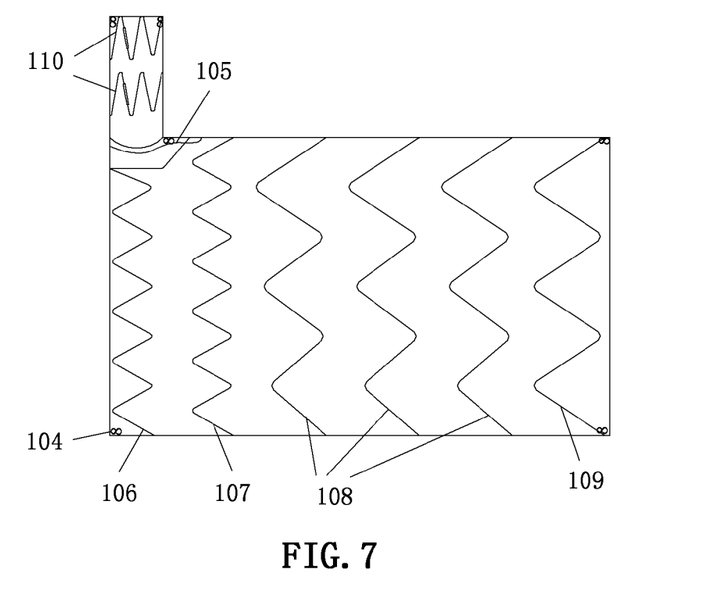
FIG. 7 is a schematic diagram of the branched stent graft of Embodiment 3.
Figure 8:
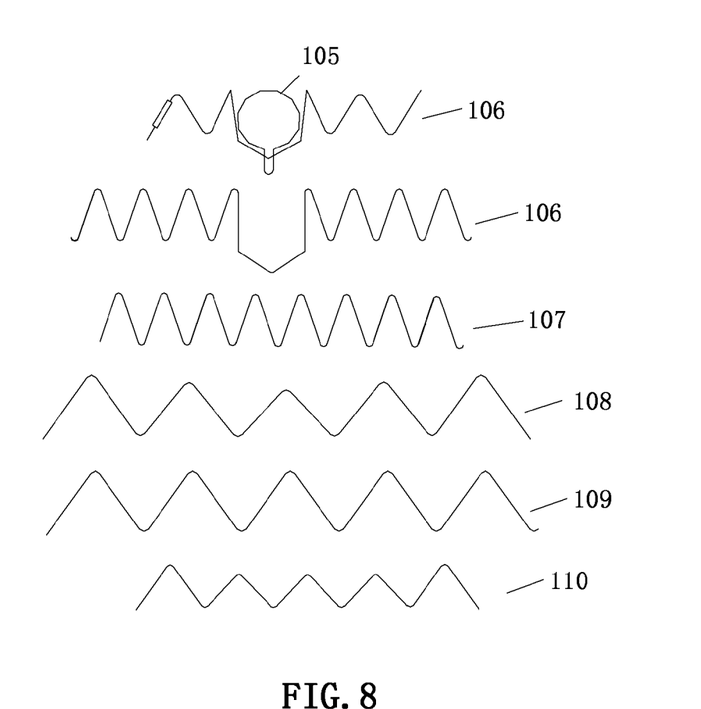
FIG. 8 is a schematic diagram of the stent segments of the branched stent graft of Embodiment 3 after expansion.

Large-Size Single Branched Stent Graft (See FIGS. 7 and 8)

Main Body Portion

Figure 9:
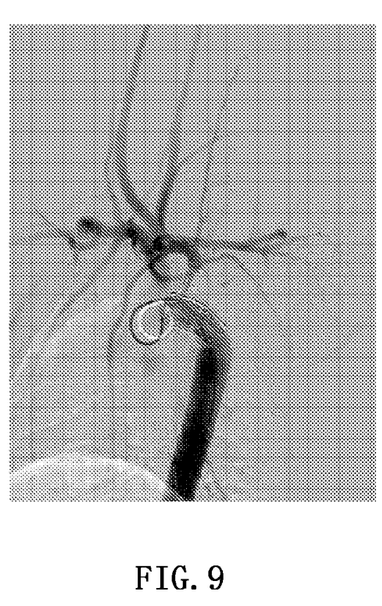
FIG. 9 is an angiography diagram of the animal experiment of the branched stent graft of Embodiment 1.

The graft of the main body is made of a polyester textile, and has a length of 110 mm and a diameter of 36 mm. The stent of the main body includes six stent segments and is made of NiTi wires, wherein the proximal two segments of the segments of the main body have a diameter of 0.018" (the left of the figure is the proximal end of the main body), and the remaining four segments have a diameter of 0.020". These six stent segments are in turn a first equal-height small wave segment 106, an equal-height small wave segment 107, three varying-height large wave segments 108, and an equal-height tail segment 109 from the proximal end to the distal end. The expansion diagrams of these stent segments are shown in FIG. 9. The first equal-height small wave segment 106 includes eight waveforms, wherein the height difference between the wave crest and the wave trough is 12 mm, the distance between the intermediate two vertex is 10 mm, and the included angle between the lower two edges is 120 degrees. The equal-height small wave segment 107 includes eight waveforms, wherein the height difference between the wave crest and the wave trough is 12 mm. The varying-height large wave segment 108 includes five waveforms, wherein with respect to the two waveforms at both ends, the height difference between the wave crest and the wave trough is 19 mm, with respect to the second and the fourth waveforms, the height difference between the wave crest and the wave trough is 17 mm, and with respect to the third waveform, the height difference between the wave crest and the wave trough is 15 mm. The equal-height tail segment 109 includes five waveforms, wherein the height difference between the wave crest and the wave trough is 19 mm. The joint of the proximal branch and the main body is provided with a positioning ring 105, which is made of NiTi wires, has a diameter of 10 mm, and is flush with the proximal end of the main body. The position of the positioning ring 105 is shown in FIG. 9. Each of the stent segments of the main body is sutured inside the graft of the main body, and the distance between the stent segments is 4 mm. The distal and proximal ends of the main body are sutured with several radiopaque markers 104.

Branch Portion

The graft of the branch is made of a polyester textile, and has a length of 30 mm and a diameter of 10 mm. The stent of the branch is made of NiTi wires and has a diameter of 0.014". The stent of the branch includes two varying-height stent segments 110 (the top of the figure is the distal end of the branch). The varying-height stent segment 110 includes five waveforms, wherein with respect to the two waveforms at both ends, the height difference between the wave crest and the wave trough is 12 mm, and with respect to the intermediate three waveforms, the height difference between the wave crest and the wave trough is 10 mm. The distance between the stent segments of the branch is 3 mm, the proximal-most stent segment of the branch is 4 mm away from the main body portion, the varying-height stent segment 110 is sutured outside the graft of the branch, and the branch is flush with the proximal end of the main body. The branch is sutured with several radiopaque markers 104.

Embodiment 4

Animal Experiments

Experimental Animal: Pigs, About 30 Kg, Half of the Pigs Being Female and Half Being Male Thirty-two experiments were performed using the single branched stent graft of Embodiment 1., in which the stent graft was applied to the left subclavian artery and a total of twenty-eight pigs survived. FIG. 9 shows the development result of the operation. It can be seen from FIG. 9 that the stent is completely expanded, the developments of the respective arteries are clear, and the blood flow in the branch and the aorta is steady.

Figure 10:
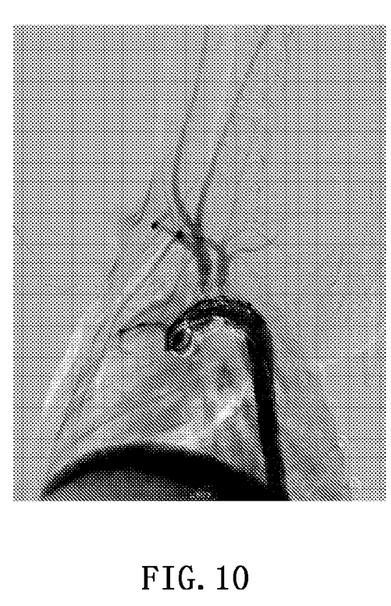
FIG. 10 is an angiography diagram of the animal experiment of the branched stent graft of Embodiment 2.

The double branched stent graft of Embodiment 2 performs four animal experiments in all, and is applied to the brachiocephalic and the left subclavian artery, wherein three pigs survive. FIG. 10 shows the development results of the operation. It can be seen from FIG. 10 that the stent is completely expanded, the developments of the respective arteries are clear, and the blood flow in the branch and the aorta is steady.

Figure 11:
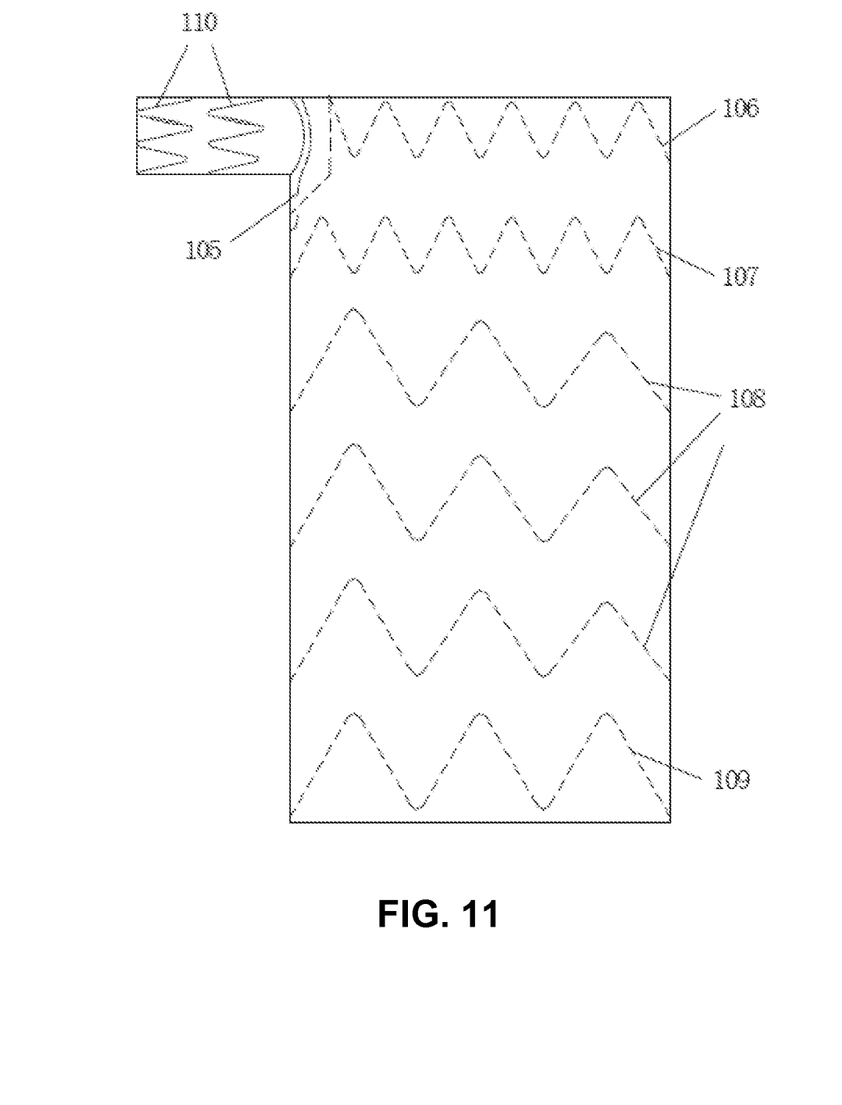
FIG. 11 is a schematic diagram of a branched stent graft with the stent segments of the branch portion sutured outside the graft and the stent segments of the main body portion sutured inside the graft.
Figure 12:
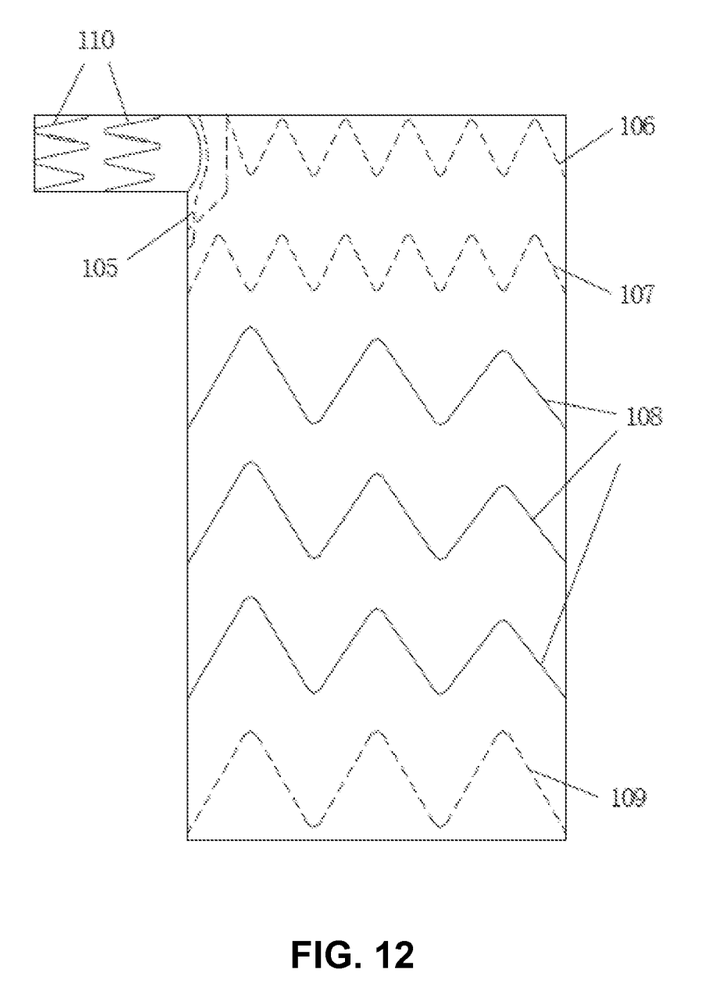
FIG. 12 is a schematic diagram of a branched stent graft with the stent segments of the branch portion and the stent segments of the main body portion all sutured inside the graft.

In FIGS. 11 and 12, the stent segments shown in dotted lines are sutured inside the graft, while the stent segments shown in solid line are sutured outside the graft. FIG. 11 shows stent segments 110 of the branch portion that are sutured outside the graft and stent segments 106, 107, 108, 109 of the main body portion that are sutured inside the graft. FIG. 12 shows stent segments 110 of the branch portion that are sutured outside the graft and the proximal and distal stent segments 106, 107 and 109 of the main body portion that are sutured inside the graft but the intermediate stent segments 108 of the main body portion are sutured outside the graft.

The invention claimed is:

1. A branched stent graft, comprising a main body portion and a branch portion, each of the main body portion and the branch portion including a stent and a tubular graft sutured with the stent, and the graft of the branch portion being sutured with the graft of the main body portion,
characterized in that:
the stent of the main body portion includes a plurality of stent segments, at least one of which is a varying-height stent segment;
the stent of the branch portion includes one or more stent segments, at least one of which is a varying-height stent segment, and
the distance between the proximal-most stent segment of the branch portion and the main body portion is in the range of 2-8 mm;
wherein a proximal end of the main body portion is provided with an equal-height stent segment, and the proximal-most end of the branch portion is connected to the proximal end of the main body portion such that a plane, that is perpendicular to the longitudinal axis of the main body, is both tangent to the branch portion and flush with the proximal-most end of the main body.

2. The branched stent graft according to claim 1, characterized in that:
a waveform of the varying-height stent segment of the main body portion and/or the branch portion after a cylindrical single coil forming the stent segment is deployed is substantially sinusoidal.

3. The branched stent graft according to claim 2, characterized in that:
the main body portion includes at least one additional equal-height stent segment,
wherein the equal-height stent segment refers to a stent segment, in which, after a cylindrical single coil forming the stent segment is deployed, all the wave troughs of the waveform thereof are on the same horizontal line, and all the wave crests are also on the same horizontal line.

4. The branched stent graft according to claim 3, characterized in that:
the distal-most stent segment of the main body portion is the equal-height stent segment.

5. The branched stent graft according to claim 4, characterized in that:
the stent segment(s) of the branch portion is(are) sutured outside the graft, and
the stent segments of the main body portion are sutured inside the graft, or the proximal and distal stent segments of the main body portion are sutured inside the graft but the intermediate stent segment(s) of the main body portion is(are) sutured outside the graft.

6. The branched stent graft according to claim 5, characterized in that:
   the graft of the main body portion has a length in the range of 40-133 mm and a diameter in the range of 16-36 mm;
   the number of the stent segments of the main body portion is in the range of 3-7, wherein a distance between the stent segments is in the range of 1-5 mm;
   the graft of the branch portion has a length in the range of 13-30 mm and a diameter in the range of 6-14 mm;
   the number of the stent segments of the branch portion is in the range of 1-2, wherein a distance between the stent segments is in the range of 1-5 mm; and
   the distance between the proximal-most stent segment of the branch portion and the main body portion is in the range of 2-4 mm.

7. The branched stent graft according to claim 6, characterized in that:
   the main body portion and the branch portion are further sutured with radiopaque markers.

8. The branched stent graft according to claim 7, characterized in that:
   the stent is made of a shape memory alloy, a 316L medical stainless steel, a Ni-based alloy or a Co-based alloy;
   the graft is made of polytetrafluoroethylene, a polyester textile, a polyamide textile or a polypropylene textile; and
   the radiopaque markers are made of a platinum-iridium alloy, pure platinum, pure gold, a NiTi shape memory alloy or a stainless steel.

9. The branched stent graft according to any one of claims 1-8, characterized in that:
   a positioning ring is used at a side opening which connects the branch portion and the main body portion, and
   the positioning ring is sutured inside the graft of the main body, between the graft of the main body and the graft of the branch, or outside the graft of the branch.

10. The branched stent graft according to claim 9, characterized in that:
    the positioning ring is provided with a flange, and
    the flange is provided in an axial direction of the main body portion.

11. The branched stent graft according to claim 10, characterized in that:
    the positioning ring is made of nickel-titanium wires, stainless steel wires, nylon or polyurethane.

\* \* \* \* \*